US00RE46931E

(19) United States
(12) Reissued Patent
McLaughlin et al.

(10) Patent Number: US RE46,931 E
(45) Date of Reissued Patent: *Jul. 3, 2018

(54) SYSTEM FOR PHASE INVERSION ULTRASONIC IMAGING

(75) Inventors: Glen McLaughlin, San Carlos, CA (US); Ting-Lan Ji, Morgan Hill, CA (US)

(73) Assignee: SHENZHEN MINDRAY BIO-MEDICAL ELECTRONICS CO., LTD., Shenzhen (CN)

( * ) Notice: This patent is subject to a terminal disclaimer.

(21) Appl. No.: 13/105,318

(22) Filed: May 11, 2011

Related U.S. Patent Documents

Reissue of:
(64) Patent No.: 6,866,631
Issued: Mar. 15, 2005
Appl. No.: 09/872,541
Filed: May 31, 2001

(51) Int. Cl.

| | |
|---|---|
| ***A61B 8/00*** | (2006.01) |
| ***A61B 8/12*** | (2006.01) |
| ***A61B 8/14*** | (2006.01) |
| ***G01S 7/52*** | (2006.01) |
| ***G01S 15/89*** | (2006.01) |
| *G01S 15/10* | (2006.01) |

(52) U.S. Cl.
CPC ..... *G01S 7/52077* (2013.01); *G01S 7/52038* (2013.01); *G01S 15/8959* (2013.01); *G01S 15/8963* (2013.01); *G01S 7/52026* (2013.01); *G01S 15/104* (2013.01)

(58) Field of Classification Search
CPC ..... G01S 7/52077; G01S 7/52038; G01S 15/8959; G01S 15/8963; G01S 7/52026; G01S 15/104
USPC ..... 600/407, 437, 447
See application file for complete search history.

(56) References Cited

U.S. PATENT DOCUMENTS

| | | | | |
|---|---|---|---|---|
| 4,631,710 | A * | 12/1986 | Yamaguchi et al. | 367/103 |
| 4,862,892 | A * | 9/1989 | Green | 600/443 |
| 4,917,097 | A * | 4/1990 | Proudian et al. | 600/463 |
| 5,349,524 | A * | 9/1994 | Daft et al. | 600/441 |
| 5,632,277 | A * | 5/1997 | Chapman et al. | 600/443 |
| 5,833,614 | A * | 11/1998 | Dodd et al. | 600/447 |
| 6,120,448 | A * | 9/2000 | Bradley et al. | 600/443 |
| 6,213,947 | B1 * | 4/2001 | Phillips | G01S 7/52038 600/443 |

(Continued)

*Primary Examiner* — Catherine S Williams
(74) *Attorney, Agent, or Firm* — Kory D. Christensen; Polsinelli LLP

(57) ABSTRACT

A system and method for ultrasonic imaging utilizing multiple sets of transmit pulses differing in amplitude, frequency, phase, and/or pulse width. One embodiment has phase differences between the k transmit signal as $$\frac{360}{k}$$

degrees providing for constructive interference of the $k^{th}$ order harmonic pulse, while an amplitude modulation of each transmit profile is constant between sets. These sets of pulses are transmitted into media of interest and received echoes from these pulses are combined to form an averaged signal. The averaged pulses represent the net common mode signal received from each of the transmit sets. This combined signal set is used to reconstruct an ultrasound image based on broad beam reconstruction methodology.

13 Claims, 6 Drawing Sheets

(56) References Cited

U.S. PATENT DOCUMENTS 6,866,631 B2 * 3/2005 McLaughlin et al. ..... 600/437
7,396,336 B2 * 7/2008 Orszulak et al. ..... 601/2

* cited by examiner

SYSTEM FOR PHASE INVERSION ULTRASONIC IMAGING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

Not Applicable

BACKGROUND OF THE INVENTION

1. Field of the Invention

The present invention relates to ultrasound imaging, and more particularly, to a method and apparatus for improving and enhancing ultrasound images.

2. Description of the Background Art

Ultrasonic imaging is frequently used for a variety of diagnostic procedures due to its non-invasive nature, low cost, and fast response time. These qualities are especially true in medical fields where the added benefit is reducing or eliminating a patient's exposure to radiation. Typically, ultrasound imaging is accomplished by 1) generating and directing an ultrasonic beam into media under investigation; and 2) observing any resulting waves that are reflected back from dissimilar tissues and tissue boundaries within that area. The resulting waves are received as signals. These received signals are then post-processed and imaged on a screen by plotting a spot whose intensity is proportional to the amplitude of a reflected beam from a given location. Determination of location is based upon a known transmission and re-radiation rate after the ultrasonic wave is pulsed into the media under investigation.

Typically, an ultrasonic signal transmitted into the media under investigation includes a burst of sinusoidal waves of a given waveform. These sinusoidal waves are applied to a transducer and form a transmitted signal. The transmitted signal is typically in the range of 40 kHz to 50 MHz, but more commonly, in the range of 40 kHz to 1 MHz. As the transmitted signal interacts with tissue layers and boundaries between layers, the ultrasonic signal is modified by being scattered, resonated, attenuated, reflected, or transmitted.

Media under investigation are often a non-linear media such as those commonly found in the human body. Non-linear media produce harmonic frequencies in the echoed signals. These additional frequency components continue to re-radiate through and, in turn, reflect off or interact with other structures. A portion of the reflected (or echoed) signals propagates back to a receiving transducer.

Fundamental and harmonic frequencies that are impinged upon a receiving transducer includes the full signal, which must then be further processed to eliminate noise and extraneous components. The receiving transducer may be the same as a transmitting transducer, or can be completely independent. When the same transducer is used, a transmit/receive (T/R) switch connects the transducer to either the transmitter electronics or the receiver post-processing electronics. The receiving transducer accepts the echo signal plus any generated noise and furnishes these to a portion of the post-processing electronics known as a beam former. Beam formers reject noise and have either an adaptive or fixed configuration. Adaptive beam formers are designed to reject variable directional noise sources by monitoring the noise field and adjusting internal parameters to minimize the background noise. Fixed beam formers are designed to reject isotropic noise and take advantage of the directional property of the reflected signal.

Ultimately, ultrasonic images of the human body are a product of harmonic imaging. Harmonic imaging is generally associated with either visualization of tissue boundaries and densities of different media, or imaging contrast agents at harmonic frequencies. Contrast agents are typically fluid filled micro-spheres that resonate at ultrasonic frequencies. Such agents are injected into the blood stream and are carried to various parts of the body. Once these agents are pulsed at ultrasonic frequencies, harmonic echo-locator signals are generated due to the resonance produced within the micro-spheres.

While ultrasonic procedures have a distinct number of advantages over other types of diagnostic techniques, prior art methods and systems have noise problems that make it difficult to determine the exact location and proper interpretation of the received signal. Various forms of averaging techniques have been employed to reduce the noise, but averaging alone is ineffective in locating images of interest between tissues with similar densities. (Echoed signals from tissues with similar densities will indicate a uniform mass with indistinct boundaries. Averaging won't help in this situation.) These interpretation difficulties are exacerbated by the fact that many tissues in the human body have similar densities. Therefore, a method and system are needed that can effectively overcome the stated difficulties while not negating the positive benefits of ultrasound imaging systems in general.

SUMMARY OF THE INVENTION

The present invention is a system and method for generating enhanced ultrasonic images. The invention utilizes multiple ultrasonic pulses that are transmitted in an alternating fashion into media of interest. These media being imaged may be a human body or some other linear and/or non-linear media. The ultrasonic pulses are modulated in a way that may vary in amplitude, frequency, phase, or pulse width. Each set of ultrasonic pulses is out-of-phase with other ultrasonic pulses by $$\frac{360^\circ}{k},$$

where k is the number of pulse sets in the pulse sequence for a given transducer element number, n. An out-of-phase condition is a property when waveforms are of the same frequency but do not have corresponding intensity values at the same instant. The echo signals generated by the non-linear media interacting with these out-of-phase signals are measured and appropriately combined.

The present invention is based on the observation that many types of media scatter sound in a non-linear manner. With an ultrasonic imaging system based on linear-scattering media, the return signal is a time-shifted, amplitude-scaled version of the incident signal. Non-linear scattering media produce signals that cannot be produced by simple time-shifts, scaling, or summation of the signal incident to a scattering site. The phase of an ultrasound wave reflected from the boundary of a non-linear medium is altered in a manner that depends on the phase of the incident sound pulse. For example, consider the special case of two ultrasound pulses (k=2), where the phase difference between the two transmitted sound pulses differ by $$\frac{360^\circ}{k} = \frac{360^\circ}{2}$$

or 180 degrees. If the scattering site were purely linear then the received signal from each of the transmitted pulses would be the inverse of each other. These inverse signals, when averaged, would have a sum of zero. If, however, there are signals generated from a non-linear process within the media, then these signals will not be the inverse of each other and, consequently, will not sum to zero.

This non-linear property can be used to construct a system that looks at the non-linear regions within given media. For example, in one embodiment of this system, an image area is formed from three different sets of transmitted signals each differing in phase by 120 degrees. The linear reflections generated by these k=3 sets of excitation pulses will cancel each other, while the $k^{th}$ order non-linear components will not. This pulse cancellation allows an averaged set of raw received data, F(n, t), to be produced. A three-dimensional averaged set of raw received data, F(n,m,t), may also be produced where m is an element from a two-dimensional, or n×m transducer array. The data functionality is dependent on the channel (or transducer) number and time. This single set of averaged data can then be used to re-construct an image area. The image area reconstructed would represent the information generated from the third, or $k^{th}$, harmonic, generated from the scattering sites within the media.

DETAILED DESCRIPTION OF THE INVENTION

The present invention relates to the field of ultrasound imaging. This invention utilizes broad beam technology ($B^2$ Technology™) to perform image extraction of the non-linear elements of media under investigation. These media will hereinafter be referred to as media of interest. Broad beam technology defines an area under investigation at a given point in time, which is in contrast with a system utilizing a focused beam.

Figure 1:
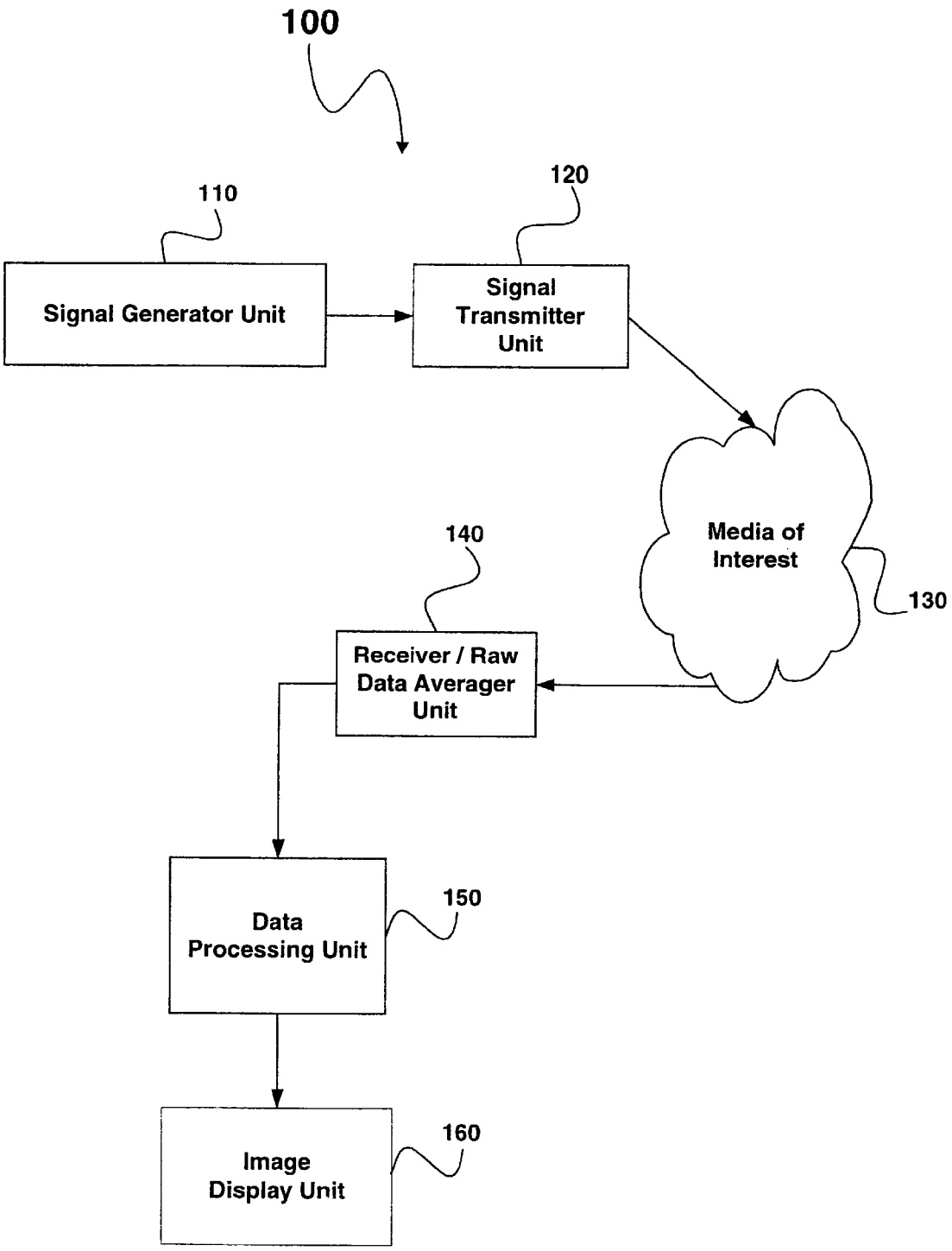
FIG. 1 is a schematic block diagram of an embodiment of an ultrasound imaging system using the present invention.

FIG. 1 is a block diagram of an embodiment of an ultrasound imaging system using the present invention. Imaging system 100 includes at least one signal generator unit 110, at least one signal transmitter unit 120, media of interest 130 to be imaged, at least one receiver and raw data averager unit 140 to capture signals received from the media of interest 130, and a data processing unit 150 for taking the averaged received signals and producing an area of image formation on an image display unit 160.

A signal generator unit 110 drives circuitry for a signal transmitter unit 120. The signal transmitter unit is shown and described in greater detail in FIG. 3.

A signal transmitter unit 120 transmits pulsed sets of ultrasonic energy into the media of interest 130. Echoes received from the media of interest 130 are stored in the receiver and raw data averager unit 140. Subsequent out-of-phase signals from the signal generator unit 110 pass through the signal transmitter unit 120, and are converted into pulsed sets of ultrasonic energy that travel to the media of interest 130. The media of interest 130 modifies the pulsed sets of ultrasonic energy. These modified pulsed sets of ultrasonic energy are received and averaged by the receiver and raw data averager unit 140. Data from these received pulsed sets are averaged in a data set as a function of channel number, n, and time, t. The averaged data sets are processed by the data processing unit 150 and displayed on an image display unit 160.

Figure 2:
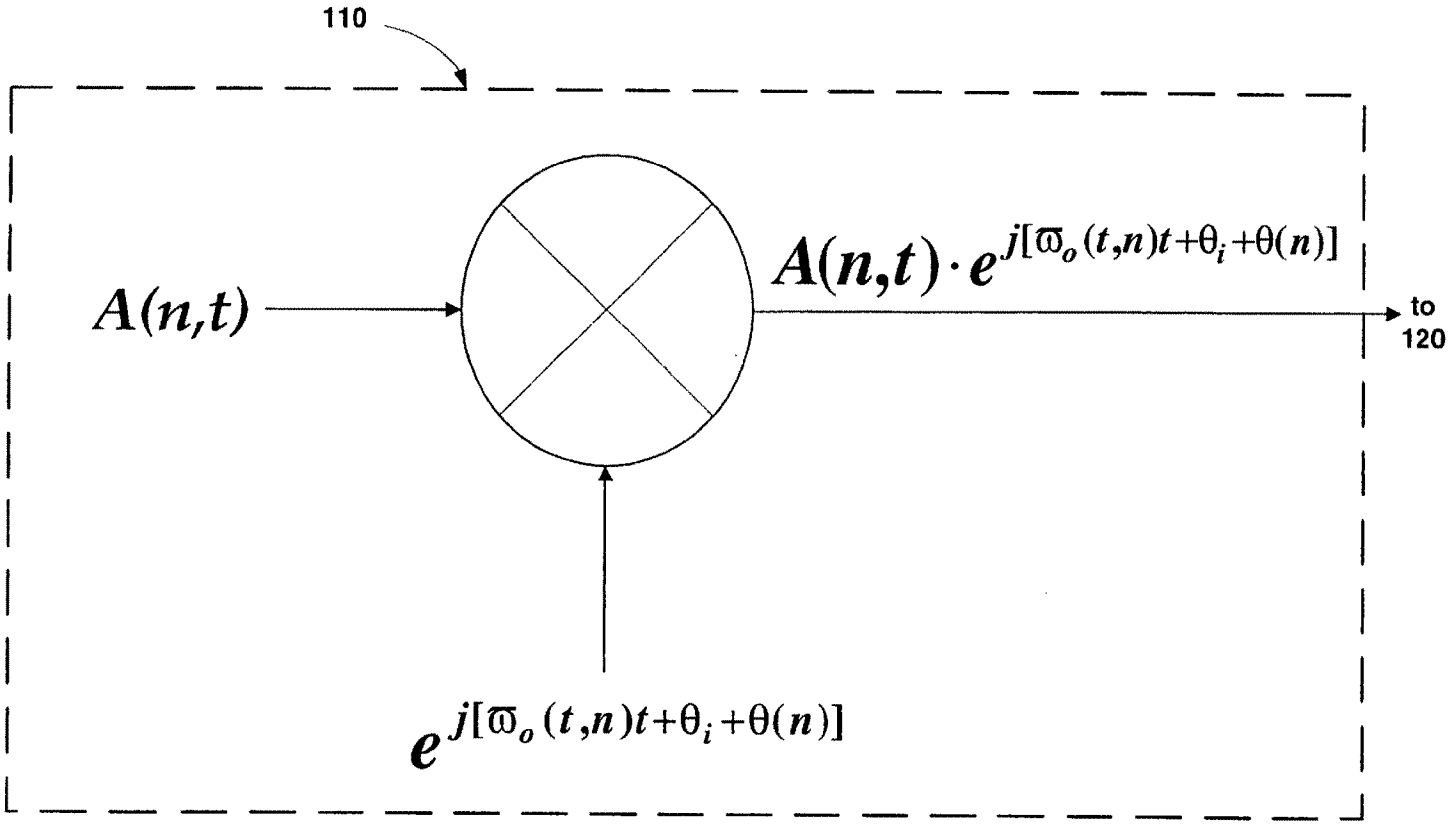
FIG. 2 shows an exemplary modification of one of a potential plurality of waveforms being modified.

FIG. 2 shows an exemplary modification of one of a potential plurality of waveforms being modified. This FIG. 2 example demonstrates how a signal generator unit 110 may modify a generated signal. For example, a stated modulation may be in the form of any combination of varying an amplitude, frequency, or pulse width of an unaffected input signal. These modulated signals will additionally vary in phase for a given pulse set. To produce a modulation, an envelope function, A(n,t), may be convolved with a sine wave, depicted by $e^{j[\omega_o(t,n)t+\theta_i+\theta(n)]}$ giving the final waveform A(n,t) $e^{j[\omega_o(t,n)t+\theta_i+\theta(n)]}$. In this waveform notation, n is the transducer element number, and i is a given pulse index (e.g., if a second harmonic is utilized, k=2, then i=1 . . . 2). The phase varies for different pulse sequences within a given pulse set and is indicated by the $\theta_i$ notation.

To illustrate the concept of phase variation, take an example where k is three. In this example, each pulse within a pulse set is varied in phase by $$\frac{360^\circ}{k} \equiv \frac{360^\circ}{3}$$

or 120°. A first pulse is generated with a 0° phase orientation, a second pulse is 120° out-of-phase with the first pulse, and a last pulse in the pulse set is 240° out-of-phase with respect to the first pulse. After the first pulse is transmitted and received, the second pulse is transmitted and received, and so on through the sequence. All information is tracked so that fundamental frequencies can be summed and eliminated, leaving primarily only harmonically generated echoes. Recall that harmonically generated echoes are produced by non-linear media.

Further, as an example, an envelope function, A(n,t), may be a Gaussian waveform. The transmitted signal may additionally be modulated as a chirped waveform (i.e., swept-frequency modulation, a Fourier transform of which is still centered around the fundamental with a broader dispersion). Optionally, a digital waveform generator could be used in place of the convolution method shown in FIG. 2.

Figure 3:
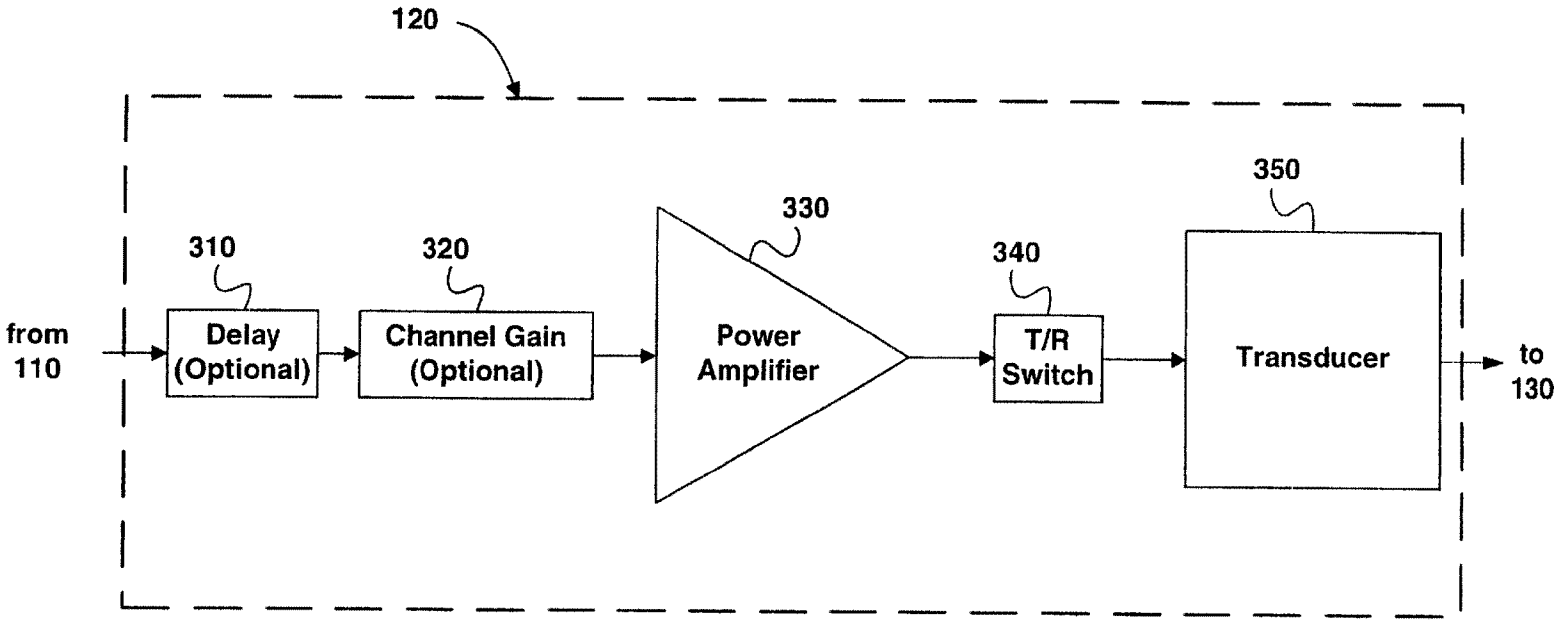
FIG. 3 shows an embodiment of a signal transmitter unit prior to signal delivery to media of interest.

FIG. 3 shows an embodiment of a signal transmitter unit 120 prior to signal delivery to media of interest. The signal transmitter unit 120 includes at least a power amplifier 330, a transmit/receive switch 340, and a first transducer 350. Optionally, a signal transmitter unit 120 may further include a delay circuit 310. The delay circuit 310 may be an analog or digital delay. Also, optionally, the signal transmitter unit 120 may include a channel gain unit 320 to drive the power amplifier 330 as a function of channel number and time. Additionally, the signal or pulse may be pulse-width modulated (not shown) to conserve power. Power conservation can become crucial in field applications of the system where battery power may be utilized.

Figure 4A:
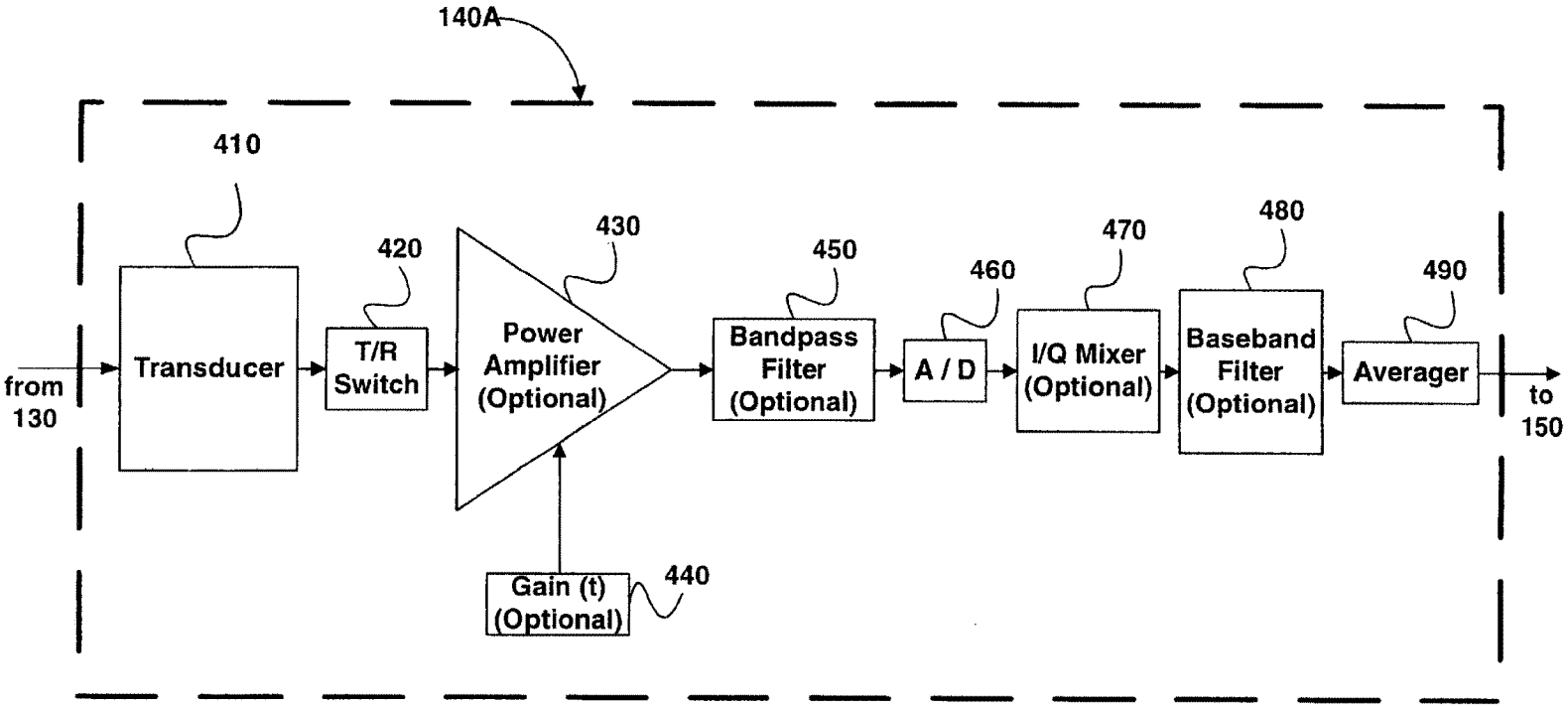
FIG. 4A shows an embodiment of a receiver and raw data averager unit.
Figure 4B:
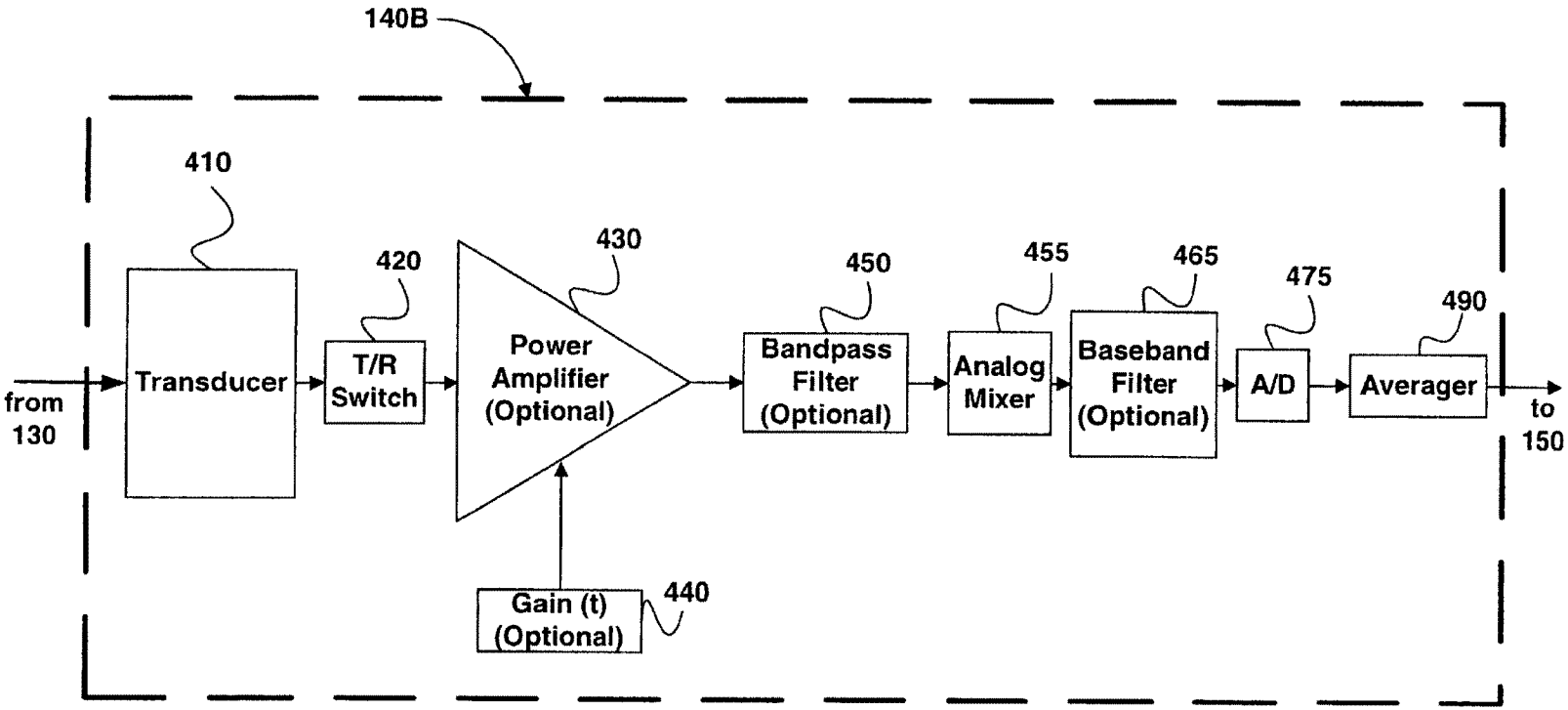
FIG. 4B shows an alternative embodiment of a receiver and raw data averager unit.

FIG. 4A shows one embodiment of a receiver and raw data averager unit 140. A second transducer 410 receives pulsed sets modified by media of interest 130. These received pulsed sets are transformed from ultrasonic energy into an electrical signal by the second transducer 410. A second transmit/receive switch 420 may be used to couple the electrical signals to the appropriate circuitry. In one embodiment, a second transducer 410 and a second transmit/receive switch 420 may be coincident or analogous units to the first transducer 350 and first transmit/receive switch 340 shown in FIG. 3. A second power amplifier 430 may be added and controlled as a function of time by gain control unit 440. The output of power amplifier 430 sends an amplified signal to an optional bandpass filter 450. The bandpass filter 450 may be used, among other things, to reduce or eliminate extraneous noise. FIGS. 4A and 4B share the same component layout up to and including bandpass filter 450, where thereafter they diverge thereby exemplifying alternate embodiments.

The electrical signal of the FIG. 4A embodiment is coupled to a first analog-to-digital (A/D) converter 460, and may continue into an optional in-phase and quadrature (I/Q) mixer 470, which produces a single side-band signal, optional first baseband filter 480, and to an averager 490. The optional first baseband filter acts to reduce or eliminate any fundamental frequency from the signals received from the original pulse sets, leaving primarily harmonically generated signals. One purpose of the averager is to provide a point-by-point arithmetic average of the received electrical signals. Mathematically, this arithmetic average may be expressed as $$F(n, t) = \sum_{i=1}^{k} \frac{R_i(n, t)}{k},$$

where the received signal, $R_i$, is summed for each element of the transmit cycle as a function of channel number and time to correlate with the original transmitted pulse, i. All other components in the signal path are of types commonly known to one of ordinary skill in the art.

FIG. 4B shows an alternative embodiment of a receiver and raw data averager unit. Recall FIGS. 4A and 4B share the same component layout through and including the optional bandpass filter 450. From the point of this optional bandpass filter 450, the signal of the FIG. 4B embodiment is further coupled to an analog mixer 455, an optional second baseband filter 465, a second analog-to-digital converter 475, and an averager 490.

Figure 5:
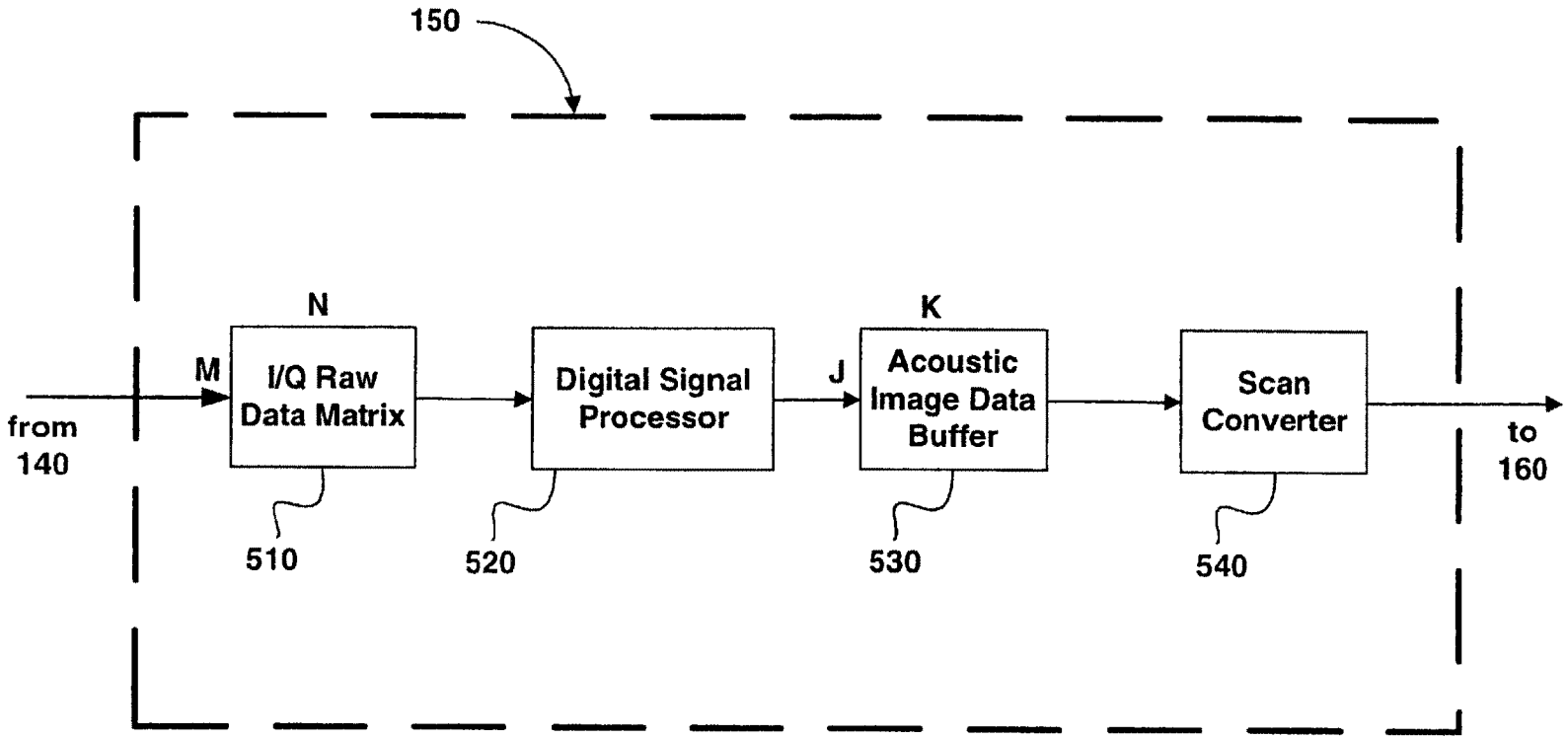
FIG. 5 shows an embodiment of a data processing unit.

FIG. 5 shows an embodiment of the data processing unit 150. Here, data processing unit 150 receives averaged data from the receiver and raw data averager unit 140. The averaged data are input to the data processing unit 150 and received at I/Q raw data matrix 510, which stores the averaged data in an M×N area array, where M is the number of samples (1 to 10,000 samples is an exemplary number) and N is the number of elements×2 (both in-phase and quadrature). These averaged data are fed into a digital signal processor (DSP) 520, which reconstructs the raw data into an area of acoustic image. An exemplary reconstruction equation may take the form of $$I(r, \varphi) = \sum_{i=1}^{k} a_i(r, \varphi) \cdot e^{j\theta_i(r,\varphi)} \cdot F[i, t_i(r, \varphi)].$$

In this equation a, indicates an aperture function, r refers to a radial distance from a transducer center at a given angle ϕ, and the function F is an averaged set of raw received data. The digital signal processor 520 functions could be achieved in any number of ways, For example, in an alternative embodiment, a properly designed application-specific integrated circuit (ASIC) could be used in place of the digital signal processor 520. These converted data in polar coordinates are saved in an acoustic image data buffer 530 in a J×K matrix (where J is the number of range samples and K is the number of angular samples). At this point, the data are still a function of a distance, r, from the transducer at a given angle, ϕ. This could also be accomplished in a Cartesian coordinate system. The acoustic image data buffer 530 allows the data to be stored until needed by scan converter 540. The I(r, ϕ) image data are converted into a reconstructed image in Cartesian coordinate data I(x,y) through the use of an r-ϕ scan converter 540. An r-ϕ scan converter is well known in the art and typically converts two-dimensional data from polar to Cartesian coordinates by means of the conversion, x=r cos(ϕ) and y=r sin(ϕ).

Output from the data processing unit 150 produces an image area I(x,y) corresponding to an area irradiated by pulsed sets of ultrasonic energy. These converted I(x,y) data may be displayed on image display unit 160. Image display unit 160 may be any visual display such as, but not limited to, a computer monitor, flat-panel or liquid-crystal display, cathode-ray tube (CRT), or the like.

From the description of the preferred embodiments of the process and apparatus set forth supra, it will be apparent to one of ordinary skill in the art that variations and additions to the embodiments can be made without departing from the principles of the present invention. For example, it could be easy to envision a system whereby an entire three-dimensional (3D) volume could be displayed at once as opposed to a two-dimensional area. This three-dimensional embodiment may be accomplished by holography or some other means. It would be an obvious extrapolation from the tenets of the two-dimensional system presented herein to construct a three-dimensional apparatus.

What is claimed is:

1. A system for ultrasonic imaging *of non-linear media*, comprising:

a signal generator unit [for generating] *that generates* at least two out-of-phase pulses, wherein [said] *the* signal generator [unit may modulate] *modulates* at least two sine waves with an envelope function to produce a modified version of [said] *the* at least two out-of-phase pulses, [said] *the* signal generator [unit] further converting [said] *the* at least two out-of-phase pulses into at least two out-of-phase acoustical pulses;

a signal transmitter [unit] coupled to [said] *the* signal generator [unit for transmitting said] *that transmits the* at least two out-of-phase acoustical pulses into media of interest;

a receiver [and] *that tracks the changes in frequency with time of the at least two out-of-phase acoustic pulses;*

*a* raw data averager [unit for receiving said] *that receives the* at least two *out-of-phase* acoustical pulses modified by [said] *the* media of interest, *and reduces a fundamental frequency of the at least two out-of phase acoustic pulses according to the tracked changes in frequency with time*; wherein data from [said] *the* at least two modified *out-of-phase* acoustical pulses are averaged [in] *to form* a data set as a function of channel number, *frequency,* and time; [and]

a data [processing unit] *processor* coupled to [said] *the* receiver and raw data averager [unit], wherein [said] *the* data [processing unit] *processor* constructs image data *for visualizing the media* from [said modified acoustical pulses,] *the averaged data; and*

*an image display, wherein* an output from [said] *the* data [processing unit] *processor* is further coupled to [an] *the* image display [unit] *to display the constructed image data for visualizing the media.*

2. The system of claim 1, wherein [said] *the* signal transmitter [unit] comprises a power amplifier *that amplifies the at least two out-of-phase acoustical pulses*, a transmit/receive switch *that selectively couples the amplified at least two out-of-phase acoustical pulses to a transducer*, and [a] *wherein the* transducer *transmits the amplified at least two out-of-phase acoustical pulses sequentially.*

3. The system of claim 2, further comprising a digital delay circuit *coupled between the signal generator and the power amplifier to delay the at least two out-of-phase acoustical pulses, and wherein the power amplifier amplifies the delayed at least two out of phase acoustical pulses.*

4. The system of claim 2, further comprising an analog delay circuit *coupled between the signal generator and the power amplifier to delay the at least two out-of-phase acoustical pulses, and wherein the power amplifier amplifies the delayed at least two out of phase acoustical pulses.*

5. The system of claim 2, further comprising a channel gain circuit *coupled between the signal generator and the power amplifier to drive the power amplifier as a function of channel number and time.*

6. The system of claim 1, wherein [said] *the* receiver and raw data averager [unit] comprises a transducer *that receives the at least two acoustical pulses modified by the media of interest*, a transmit/receive switch[,] *that couples the transducer to* an analog-to-digital converter *that digitizes the modified at least two acoustical pulses*, and an averager *that averages the digitized at least two acoustical pulses to form the data set as a function of channel number and time.*

7. The system of claim 6, wherein [said] *the* receiver and raw data averager [unit] further comprises a power amplifier *that amplifies the modified at least two acoustical pulses*, a bandpass filter *that filters the amplified at least two acoustical pulses*, and a baseband filter *that further filters the amplified at least two acoustical pulses.*

8. The system of claim 6, wherein [said] *the* receiver and raw data averager [unit] further comprises an in-phase and quadrature mixer *coupled between the power amplifier and the averager.*

9. The system of claim 1, wherein [said] *the* signal generator [unit] and [said] *the* receiver and raw data averager [unit] share a transducer *that transmits the at least two out-of-phase acoustical pulses and that receives the at least two modified acoustical pulses.*

10. The system of claim 1, wherein [said] *the* data processing [unit] comprises an in-phase and quadrature mixer *that downconverts the received at least two modified acoustic pulses from a first frequency to a second frequency*, a digital signal processor *that constructs the acoustic image data based on the side-band signal*, an acoustic image data buffer *that buffers the acoustic image data*, and a scan converter *that converts the buffered acoustic image data from a first coordinate system to a second coordinate system for display on the image display.*

11. The system of claim 1, wherein [said] *the* data [processing unit] *processor* comprises an in-phase and quadrature mixer *that downconverts the received at least two modified acoustic pulses from a first frequency to a second frequency*, an application specific integrated circuit *that constructs the acoustic image data based on the side-band signal*, an acoustic image data buffer *that buffers the acoustic image data*, and a scan converter *that converts the buffered acoustic image data from a first coordinate system to a second coordinate system for display on the image display.*

*12. A system for ultrasonic imaging of non-linear media, the system comprising:*

*a signal generator for generating at least two out-of-phase pulses, wherein the signal generator modulates at least two sine waves with an envelope function to produce a modified version of the at least two out-of-phase pulses, the signal generator further converting the at least two out-of-phase pulses into at least two out-of-phase acoustical pulses having different frequencies and different amplitudes;*

*a signal transmitter coupled to the signal generator for transmitting the at least two out-of-phase acoustical pulses into non-linear media of interest;*

*a receiver that tracks the changes in frequency with time of the at least two out-of phase acoustic pulses;*

*raw data averager for receiving the at least two out-of-phase acoustical pulses modified by the non-linear media of interest, and reducing a fundamental frequency of the at least two out-of phase acoustic pulses according to the tracked changes in frequency with time, wherein data from the at least two modified out-of-phase acoustical pulses are averaged in a data set as a function of channel number, frequency, and time; and*

*a data processor coupled to the receiver and raw data averager, wherein the data processor constructs image data for visualizing the non-linear media from the modified out-of-phase acoustical pulses; and*

*an image display, wherein an output from the data processor is further coupled to the image display to display the constructed image data for visualizing the non-linear media.*

*13. A system for ultrasonic imaging non-linear, the system comprising:*

*a signal generator for generating at least two out-of-phase pulses, wherein the signal generator modulates at least two sine waves with an envelope function to produce a modified version of the at least two out-of-phase pulses, the signal generator further converting the at least two out-of-phase pulses into at least two out-of-phase acoustical pulses having different pulse widths, and wherein each of the at least two out-of-phase acoustic pulses changes in frequency with time;*

*a signal transmitter coupled to the signal generator for transmitting the at least two out-of-phase acoustical pulses into media of interest;*

*a receiver that tracks the changes in frequency with time of the at least two out-of phase acoustic pulses;*

*raw data averager for receiving the at least two out-of-phase acoustical pulses modified by the non-linear media of interest, and reducing a fundamental fre-*

*quency of the at least two out-of phase acoustic pulses according to the tracked changes in frequency with time, wherein data from the at least two modified out-of-phase acoustical pulses are averaged in a data set as a function of channel number, frequency, and time; and*

*a data processor coupled to the receiver and raw data averager, wherein the data processor constructs image data from the modified out-of-phase acoustical pulses; and*

*an image display, wherein an output from the data processor is further coupled to the image display to display the constructed image data.*

* * * * *